United States Patent
Nakao et al.

(10) Patent No.: US 7,115,125 B2
(45) Date of Patent: Oct. 3, 2006

(54) MEDICAL CAUTERIZATION SNARE ASSEMBLY AND ASSOCIATED METHODOLOGY

(75) Inventors: Naomi L. Nakao, New York, NY (US); Peter J. Wilk, New York, NY (US)

(73) Assignee: Granit Medical Innovations, LLC, New York, NY (US)

(*) Notice: Subject to any disclaimer, the term of this patent is extended or adjusted under 35 U.S.C. 154(b) by 383 days.

(21) Appl. No.: 10/250,855

(22) PCT Filed: Jan. 11, 2002

(86) PCT No.: PCT/US02/00840

§ 371 (c)(1),
(2), (4) Date: Jul. 1, 2003

(87) PCT Pub. No.: WO02/054942

PCT Pub. Date: Jul. 18, 2002

(65) Prior Publication Data

US 2004/0059345 A1    Mar. 25, 2004

Related U.S. Application Data

(60) Provisional application No. 60/261,505, filed on Jan. 12, 2001.

(51) Int. Cl.
*A61B 18/18* (2006.01)
(52) U.S. Cl. .................................. 606/47; 606/113
(58) Field of Classification Search ............. 606/27–52
See application file for complete search history.

(56) References Cited

U.S. PATENT DOCUMENTS

| | | | |
|---|---|---|---|
| 5,201,740 A | | 4/1993 | Nakao et al. |
| 5,486,182 A | * | 1/1996 | Nakao et al. ............ 606/114 |
| 5,759,187 A | | 6/1998 | Nakao et al. |
| 6,007,546 A | * | 12/1999 | Snow et al. ............ 606/113 |
| 6,071,233 A | | 6/2000 | Ishikawa et al. |

* cited by examiner

*Primary Examiner*—Roy D. Gibson
*Assistant Examiner*—Pete Vrettakos
(74) *Attorney, Agent, or Firm*—R. Neil Sudol; Henry D. Coleman; William J. Sapone (57) ABSTRACT

A medical cauterization snare assembly with a tubular member, an electrically conductive cauterization loop ejectable from a distal end of the tubular member, and a capture pouch also ejectable from the distal end of the tubular member. The pouch is attached to an auxiliary loop which has a size larger than that of the cauterization loop. Alternatively, the tubular member is formed at its distal end with a first port or opening and in a distal end portion with a second port or opening spaced from the first port or opening. The two ports or openings both face in a distal direction (i.e., away from the user). The cauterization loop is alternately ejectable from and retractable into the first port or opening, while the capture pouch is separately ejectable from the second port or opening. Alternatively, the capture pouch is attached to the cauterization loop, to only a proximal portion of the loop to divide the loop's area into a proximal section covered by the pouch and an open or uncovered distal section.

16 Claims, 3 Drawing Sheets

MEDICAL CAUTERIZATION SNARE ASSEMBLY AND ASSOCIATED METHODOLOGY

FIELD OF THE INVENTION

This invention relates to a surgical instrument assembly for use in removing and retrieving selected tissues from internal body cavities of a patient. This invention more specifically relates to an instrument assembly for use in snare cauterization operations. This invention also relates to an associated method for severing internal organic tissues and retrieving the severed organic tissues from the patient. The invention is particularly useful in the removal of polyps, for example, from the colon of a patient.

BACKGROUND OF THE INVENTION

In a conventional endoscopic snare operation, an endoscope is inserted into an internal cavity of a patient, e.g., into the colon, and is used to locate abnormal tissue growths such as polyps in the internal cavity. Upon the locating of a polyp or other growth which is to be removed, a wire extending through a tube in the biopsy channel of the endoscope is slid in the distal direction so that a cauterization loop connected to the wire is ejected from the distal end of the tube and the endoscope. The loop and the endoscope are manipulated from outside of the patient to pass the loop over the polyp or growth. The wire is then withdrawn in the proximal direction to tighten the loop around a base region or neck of the polyp. Once the loop is in contact with the base region of the polyp, an electrical current is conducted through the loop via the wire. Generally, as the loop is closed about the base region of the polyp, electrical current is transmitted through the narrowed organic tissues and thereby generates therein heat sufficiently great to cut and cauterize.

Once a polyp is severed by such a snare cauterization technique, it frequently becomes difficult to capture the polyp and retrieve it from the patient. Sometimes the cauterization loop is used in an effort to ensnare the polyp. Other capture techniques involve the use of forceps or the application of suction. In using forceps, the snare cauterization tube is removed from the biopsy channel of the endoscope and replaced with the forceps. In using suction, a vacuum is applied via a suction channel of the endoscope.

No matter which specific technique is used, the polyp frequently escapes from the capturing instrumentality and falls away into the colon (or other cavity). Especially in cases where the polyp is large, the effort and time expended in retrieving the severed polyp may rival or even exceed the effort and time required to locate and sever the polyp. In some cases, the endoscope must be removed without the polyp and the patient given an enema in an attempt to flush out the polyp from the colon.

Furthermore, there are numerous cases where a severed polyp is never recovered. Sometimes, the polyp is macerated during the retrieval attempt. In all such cases, the pathologist is unable to determine whether the polyp contains carcinoma in situ (localized) or infiltrative carcinoma (spread). The patient must then undergo a colon resection, sometimes unnecessarily.

In any event, the manipulations necessary to remove a severed polyp generally increase the trauma to the patient, the expense of the surgery and the hospitalization time. There is now a long-felt need to improve the snare cauterization technique to facilitate the capture and retrieval of severed polyps.

U.S. Pat. No. 5,201,740 to Nakao et al. provides a solution to the above-described problems in polyp removal. Pursuant to the disclosure of that patent, snare cauterization operations are performed with a surgical instrument assembly comprising a tubular sheath member carrying a metallic cauterization loop and a metal wire operatively connected to the loop, the wire passing longitudinally through the sheath. An electrical supply is operatively connectable to the wire, while a flexible web member is connected to the loop to form a capture pocket, the loop defining a mouth opening of the pocket. During use of the snare cauterization loop, the web member is passed over and substantially surrounds a polyp. The pocket captures the polyp at the same time that the cauterization loop is energized to effectuate a severing of the polyp.

This cauterization snare assembly with attached pocket is a substantial advance over conventional polyp removal techniques. However, the snare assembly is generally useful for collecting only one polyp from a patient. Owing to the cumulative heating of the points of attachment of the capture pouch to the cauterization loop, the capture pouch can be separated from the cauterization loop after polyp capture has occurred. Thus, where the patient has multiple polyps, multiple cauterization snare assemblies must be used.

OBJECTS OF THE INVENTION

An object of the present invention is to provide an improved instrument assembly for the removal of polyps and other organic tissue parts from patients, particularly an instrument assembly useful for removing multiple polyps from a patient's colon.

Another particular object of the present invention is to provide such an instrument assembly which is simple to manufacture and therefore inexpensive.

A further particular object of the present invention is to provide such an instrument assembly which is easy to use.

Yet another object of the present invention is to provide an associated method for the removal of tissue samples from a patient.

These and other objects of the present invention will be apparent from the descriptions and drawings herein. It is to be noted that each object is attained by one or more embodiments of the invention. No single embodiment, however, need attain all objects stated implied herein.

SUMMARY OF THE INVENTION

The present invention is directed to a medical cauterization snare assembly comprising a tubular member, an electrically conductive cauterization loop ejectable from a distal end of the tubular member, and a capture pouch also ejectable from the distal end of the tubular member. In one embodiment of the invention, the pouch is attached to an auxiliary loop which has a size larger than that of the cauterization loop so that a simultaneous retraction of the two loops into the distal end of the tubular member results in a completed contraction of the cauterization loop while a portion of the auxiliary loop still remains outside of the tubular member.

The difference in the sizes of the cauterization loop and the auxiliary loop minimize contact between the loops and thus reduces the transmission of heat energy to the auxiliary loop and the pouch. It is to be noted that a severed polyp is easily captured by a pouch even if the pouch is partially opened. The severed polyp is small and light and is easily entrained by a partially closed pouch.

In a more particular embodiment of the present invention, the cauterization loop and the auxiliary loop are both connected to a common wire slidably extending through the tubular member. Thus, both loops are ejected and retracted by manipulation of a single wire. Preferably, at least a portion of the auxiliary loop is made of a heat resistant material such as nylon Pursuant to another feature of the present invention, the cauterization loop and the auxiliary loop are at least approximately coplanar in the expanded configuration they assume upon ejection from the tubular member. Generally, the loops are biased by internal spring forces to assume the expanded configuration. When disposed inside the tubular member, the loops are held in a contracted configuration.

Pursuant to another feature of the present invention, the auxiliary loop is bent out of a planar configuration. Thus, the expanded auxiliary loop may have a cup shaped form partially coplanar with the cauterization loop and partially projecting from the plane of the cauterization loop.

A related medical cauterization snare assembly comprises, in accordance with the present invention, a tubular member, an elongate electrically conductive element slidably disposed at least partially in the tubular member, and a cauterization loop made of an electrically conductive material and provided at one end of the electrically conductive element for alternate ejection from and retraction into a distal end of the tubular member. The snare assembly additionally comprises an auxiliary loop larger than the cauterization loop, an elongate connector element, and a pouch member. The auxiliary loop is formed at one end of the connector element whereby the auxiliary loop is alternately ejected from and retracted into the tubular member. The pouch member is attached to the auxiliary loop so as to form a capture pocket with the auxiliary loop defining a mouth or opening of the capture pocket.

The electrically conductive element generally takes the form of a wire, while the connector element may be a stiff fiber or thread fastened at a proximal end to the wire and connected at a distal end to the auxiliary loop. Whereas the wire has a length on the order of one-half meter to one meter, the fiber or thread is preferably connected to the wire at a point spaced only a few centimeters from the proximal end of the cauterization loop.

An associated minimally invasive surgical method utilizes the above-described cauterization snare assembly and comprises inserting a distal end portion of the tubular member into a patient and thereafter pushing the electrically conductive element to eject the cauterization loop from the tubular member, the cauterization loop expanding from a collapsed configuration into an at least partially opened configuration upon ejection of the cauterization loop from the tubular member. The method also comprises pushing the connector element to eject the auxiliary loop from the tubular member after the inserting of the distal end portion of the tubular member into the patient. Upon this ejection, the auxiliary loop expands from a collapsed configuration into an at least partially opened configuration. Thereafter the tubular member and the electrically conductive element are manipulated to pass the expanded cauterization loop and the expanded auxiliary loop over a lump of tissue inside the patient. Then the electrically conductive element and the connector element are pulled to simultaneously draw the cauterization loop and the auxiliary loop into the distal end portion of the tubular member, thereby contracting the cauterization loop and the auxiliary loop. An electrical current is passed through the cauterization loop during the pulling of electrically conductive element and the connector element and the contracting of the cauterization loop and the auxiliary loop, thereby severing the lump of tissue. The severed lump of tissue is caught in the capture pocket upon a partial closure thereof owing to drawing of the auxiliary loop into the distal end portion of the tubular member. A portion of the auxiliary loop remains outside of the tubular member after the cauterization loop has been completely withdrawn into the distal end portion of the tubular member.

In a second embodiment of a medical cauterization snare assembly in accordance with the present invention, the tubular member is formed at its distal end with a first port or opening and in a distal end portion with a second port or opening spaced from the first port or opening. The two ports or openings both face in a distal direction (i.e., away from the user). The cauterization loop is alternately ejectable from and retractable into the first port or opening, while the capture pouch is separately ejectable from the second port or opening.

In this second embodiment of the invention, the spacing between the ports or openings at the distal end of the tubular member facilitates the ejection and placement of the capture pouch after the cauterization loop has been positioned over a target tissue lump. It is to be noted again that a severed polyp is easily captured by a pouch even if the pouch is still open. Thus, placement of an open pouch over the polyp in using this second embodiment of the invention is adequate to entrain the polyp after severing thereof by the cauterization loop.

In the second embodiment of the present invention, the tubular member is preferably formed with a partition member dividing a lumen of the tubular member into a first channel and a second channel. The first channel communicates with the first port or opening, while the second channel communicates with the second port or opening. The wire to which the cauterization loop is connected slidably extends through the first channel, whereas the elongate member to which the pouch is attached slidably traverses the second channel.

A medical cauterization snare assembly incorporating this second embodiment of the present invention comprises a tubular member provided at a distal end with a first port or opening and in a distal end portion with a second port or opening spaced from the distal end, the first port or opening and the second port or opening facing in a distal direction. The cauterization snare assembly further comprises an elongate electrically conductive element (e.g., wire) slidably disposed at least partially in the tubular member, a cauterization loop made of an electrically conductive material and provided at one end of the electrically conductive element for alternate ejection from and retraction into the distal end portion of the tubular member via the first port or opening. An elongate slider element is slidably disposed at least partially in the tubular member, and an auxiliary loop is provided at one end of the elongate slider element for alternate ejection from and retraction into the distal end portion of the tubular member via the second port or opening. A pouch is attached to the auxiliary loop so as to form a capture pocket with the auxiliary loop defining a mouth or opening of the capture pocket. As discussed above, the tubular member is preferably formed with a partition member dividing a lumen of the tubular member into a first channel and a second channel, the first channel communicating with the first port or opening, the second channel communicating with the second port or opening, the electrically conductive element slidably extending through the first channel, the elongate slider element slidably extending through the second channel.

In accordance with another aspect of the present invention, the tubular member of the second embodiment of the invention is provided on a surface of the partition member between the first port or opening and the second port or opening with a visually perceptible marker. The marker is exemplarily a red spot. The marker is used as a visual cue to alert the user as to the orientation of the distal end portion of the tubular member and, accordingly, the orientation of the pouch.

The various embodiments of the present invention preferably include a tether or string provided on the capture pouch for facilitating a closure of the pouch about a severed polyp.

In a third embodiment of a medical cauterization snare assembly in accordance with the present invention, there is no auxiliary loop. Instead, the capture pouch is attached to the cauterization loop. The cauterization loop in the opened or expanded configuration defines or bounds an area. The pouch is attached to only a proximal portion of the loop to divide the loop's area into a proximal section covered by the pouch and an open or uncovered distal section. Essentially, only the exposed part of the cauterization loop does the cutting and generates heat. Accordingly, the pouch is not unduly heated and remains attached to the cauterization loop after completion of a polyp retrieval operation. The instrument assembly may then be reinserted into a patient (e.g., through the biopsy channel of an endoscope).

Pursuant to another feature of the present invention, the pouch of this third embodiment is fixed to the cauterization loop at a pair of opposed points on the loop. A rim of the pouch extends across the open cauterization loop from one side thereof to another.

DESCRIPTION OF THE PREFERRED EMBODIMENTS

Figure 1:
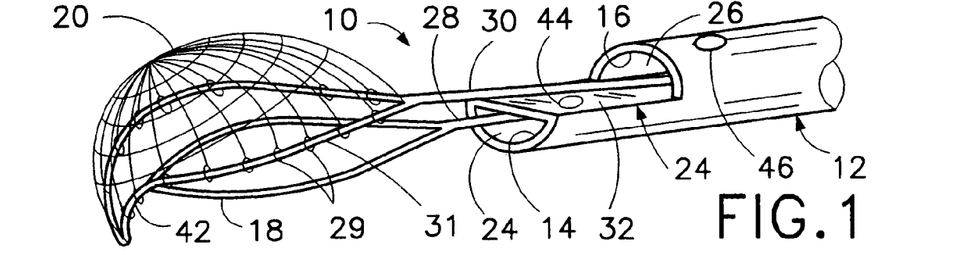
FIG. 1 is a schematic perspective view of a cauterization snare assembly in accordance with the present invention.

As illustrated in FIG. 1, a cauterization snare assembly 10 comprises a tubular member 12 formed at its distal end with a first port or opening 14 and in a distal end portion with a second port or opening 16 spaced from the first port or opening. The two ports or openings 14 and 16 both face in a distal direction (i.e., away from the user). A cauterization loop 18 is alternately ejectable from and retractable into port or opening 14, while a capture pouch 20 is separately ejectable from port or opening 16.

Tubular member 12 is preferably formed with a partition member 22 dividing a lumen (not separately designated) of the tubular member into a first channel 24 and a second channel 26. Channel 24 communicates with port or opening 14, while channel 26 communicates with port or opening 16. Cauterization loop 18 is made of an electrically conductive material and is connected to an elongate electrically conductive element in the form of a wire 28 slidably extending through channel 24. Wire 28 serves not only to carry electrical current to cauterization loop 18 but also functions to transmit mechanical compressive and tensile forces to enable an alternating ejection and retraction of the cauterization loop. Similarly, pouch 20 is attached to an elongate actuator element 30 which slidably traverses channel 26 and enables a user to eject pouch 20 from channel 26 and alternately withdraw the ejected pouch back into channel 26. More specifically, pouch 20 is attached via metal ringlets 29 to an auxiliary loop 31 provided at the distal end of actuator element 30. Auxiliary loop 31, as well as fibers of pouch 20, is preferably made of a heat-resistant material such as nylon. Alternatively, auxiliary loop 31 may be made of metal having a coating of a heat resistant material such as nylon.

Ports or openings 14 and 16 are spaced from one another by a section 32 of partition member or divider 22 which forms a shelf or an outer wall of the distal end portion of tubular member 12 and which partially defines or encloses the distal end portion of channel 24. The spacing between ports or openings 14 and 16 facilitates the ejection and placement of capture pouch 20 after cauterization loop 18 has been positioned over a target tissue lump PLP (FIGS. 2A–2E). It is to be noted again that a severed polyp PLP is easily captured by pouch 20 even if the pouch is still open. Thus, placement of an open pouch 20 over the polyp PLP in using the cauterization snare assembly 10 of FIG. 1 is adequate to entrain the polyp after severing thereof by cauterization loop 18.

Figure 2A:
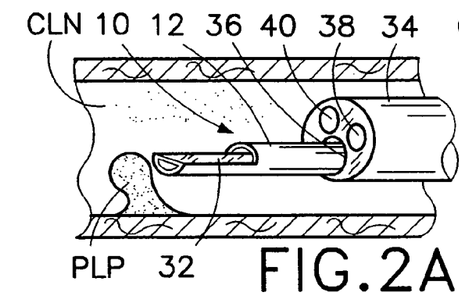
FIGS. 2A through 2E are partially cross-sectional views of a patient's colon and partially schematic perspective views of an endoscope employing the cauterization snare assembly of FIG. 1, showing successive steps in a polyp retrieval method pursuant to the invention.
Figure 2B:
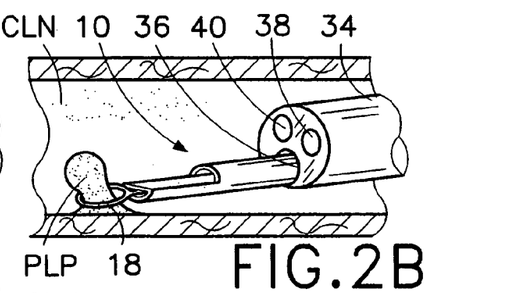
Figure 2C:
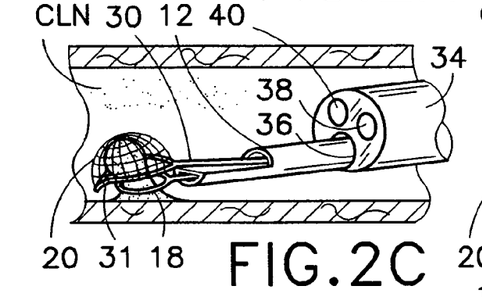
Figure 2D:
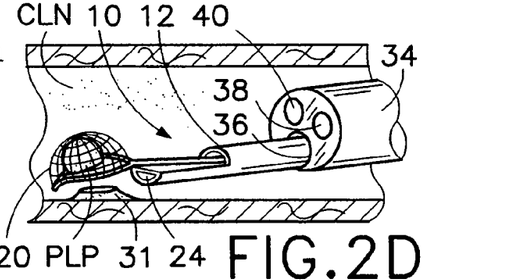

FIG. 2A depicts a distal end portion of an endoscope insertion member 34 inserted into a patient's colon CLN. Tubular member 12 is disposed in a biopsy channel 36 of endoscope insertion member 34. Light emitted by illumination optics 38 is reflected or scattered by the internal tissues of colon CLN. The reflected or scattered light is detected via additional optics including a lens 40. Upon a visual detection of polyp PLP, tubular member 12 is pushed in a distal direction, towards polyp PLP, so that ports or openings 14 and 16 are disposed outside of biopsy channel 36, as shown in FIG. 2A. Then wire 28 is pushed in the distal direction through channel 24 so that cauterization loop 18 is ejected through port or opening 14. Endoscope insertion member 34, tubular member 12 and/or wire 28 is then manipulated to position cauterization loop 18 over polyp PLP, as shown in FIG. 2B. Elongate actuator element 30 is subsequently shifted in the distal direction to eject auxiliary loop 31 and pouch 20 from channel 26 through port or opening 16, as illustrated in FIG. 2C. Endoscope insertion member 34, tubular member 12 and/or actuator element 30 is then manipulated to position auxiliary loop 31 over polyp PLP (FIG. 2C.) Cauterization loop 18 is then retracted back into channel 24 via port or opening 14, by a pulling of the wire 28 in the proximal direction. An electrical current is passed through cauterization loop 18 via wire 28 during the pulling of the wire and the contracting of cauterization loop 18, thereby severing polyp PLP, as depicted in FIG. 2D. The severed polyp PLP is entrained by pouch 20, which is then drawn in a proximal direction back towards port or opening 16. The entire instrument assembly, including endoscope insertion member 34, tubular member 12, actuator element 30, auxiliary loop 31 and pouch 20, is then removed from the patient's colon CLN. The instrument assembly may be used again to extract further polyps (not shown) from the patient.

It is to be noted, as discussed in detail hereinafter, that auxiliary loop 31 may be turned or bent, particularly at a distal end 42 (FIG. 1), to facilitate capture of polyp PLP. Also, a mark such as a red spot 44 or 46 may be provided on a distal end of tubular member 12 to facilitate detection of the angular orientation of tubular member 12 about its longitudinal axis.

Figures 2E, 3:
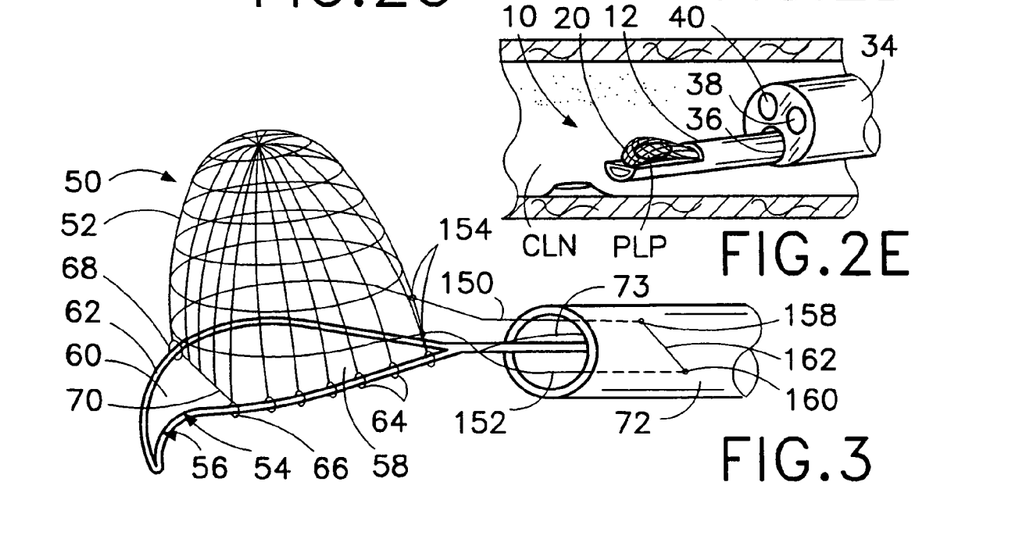
FIG. 3 is a schematic perspective view of another cauterization snare assembly in accordance with the present invention.

A medical cauterization snare assembly 50 as illustrated in FIG. 3 has no auxiliary loop. Instead, a capture pouch or basket 52 is attached to a cauterization loop 54. Cauterization loop 54 in the opened or expanded configuration defines or bounds a generally almond-shaped area 56. Pouch 52 is attached to only a proximal portion of cauterization loop 54 to divide the loop's area 56 into a proximal section 58 covered by the pouch and an open or uncovered distal section 60. Essentially, only an exposed part 62 of cauterization loop 54 implements tissue cutting and generates heat. Accordingly, pouch 52 is not unduly heated and remains attached to cauterization loop 54 after completion of a polyp retrieval operation. The cauterization snare instrument assembly 50 may then be reinserted into a patient.

Pouch 52 is attached to cauterization loop 54 via a plurality of ringlets 64. At two opposed points 66 and 68, pouch 52 is fixedly secured to loop 54. A rim 70 of pouch 52 extends across the open cauterization loop 54 from one side thereof to another. Ringlets 64 may be slidably attached or fixedly coupled to loop 54. In the former case, a string (not shown) may be connected to a proximal end of the pouch to ensure a reopening thereof upon an ejection of the cauterization loop 54 and pouch 52 from a distal end of a tubular member 72 upon a pushing of an elongate actuator element or wire 73.

Figure 4A:
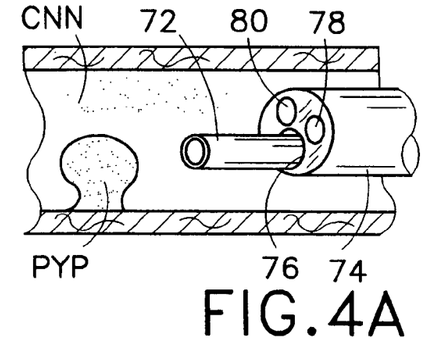
FIGS. 4A through 4D are partially cross-sectional views of a patient's colon and partially schematic perspective views of an endoscope employing the cauterization snare assembly of FIG. 3, showing successive steps in a polyp retrieval method pursuant to the invention.
Figure 4B:
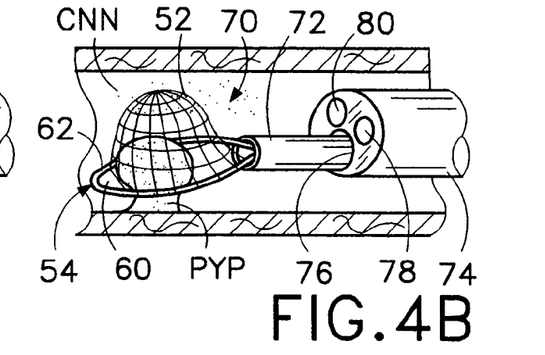
Figure 4C:
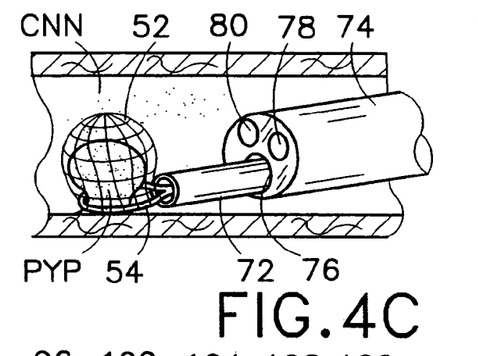
Figure 4D:
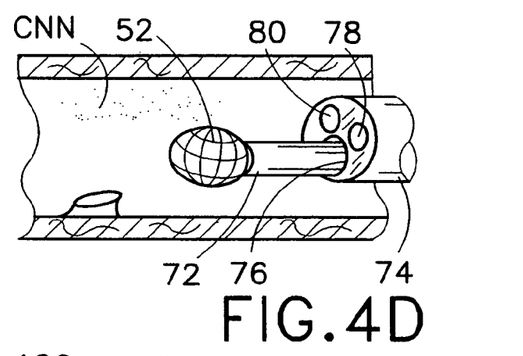

FIG. 4A depicts a distal end portion of an endoscope insertion member 74 inserted into a patient's colon CNN. Tubular member 72 is disposed in a biopsy channel 76 of endoscope insertion member 74. Light emitted by illumination optics 78 is reflected or scattered by the internal tissues of colon CNN. The reflected or scattered light is detected via additional optics including a lens 80. Upon a visual detection of a polyp PYP, tubular member 74 is shifted in a distal direction, towards polyp PYP, so a distal end portion of the tubular member 74 is disposed outside of biopsy channel 76, as shown in FIG. 4A. Wire 73 is then shifted in the distal direction through tubular member 72 to eject pouch 52 and cauterization loop 54. Upon ejection from tubular member 72, cauterization loop 54 (as well as all other loops disclosed herein) expands from a substantially closed or collapsed storage configuration inside the tubular member to an opened used configuration outside of the tubular member, the loop being formed with an inherent spring bias tending to form the loop into the opened configuration. Endoscope insertion member 74, tubular member 72 and/or wire 73 is subsequently manipulated to position cauterization loop 54 and pouch 52 over polyp PYP, as shown in FIG. 4B. After that positioning of the loop 54 and pouch 52, wire 73 is pulled in a proximal direction so that cauterization loop 54 closed about polyp PYP (FIG. 4C) and is electrically energized so that exposed port 62 of the cauterization loop cuts and cauterizes the polyp (FIG. 4D). The entire instrument assembly, including endoscope insertion member 74, tubular member 72, cauterization loop 54 and pouch 52, is then removed from the patient's colon CNN. The instrument assembly may be used again to extract further polyps (not shown) from the patient. That portion of loop 54 surrounding proximal section 58 may be coated with a heat-resistant material such as nylon to inhibit separation of pouch 52 from loop 54. In addition, ringlets 64 may be made of a heat-resistant material such as polytetraflouroethylene which is not heat conductive.

Figure 5:
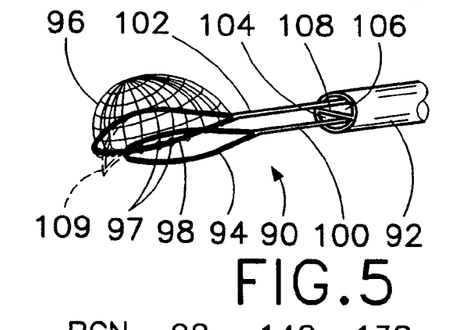
FIG. 5 is a schematic perspective view of a further cauterization snare assembly in accordance with the present invention.

As depicted in FIG. 5, another medical cauterization snare assembly 90 comprises a tubular member 92, an electrically conductive cauterization loop 94 ejectable from a distal end of the tubular member, and a capture pouch 96 also ejectable from the distal end of the tubular member. Pouch 96 is attached via ringlets 97 to an auxiliary loop 98 which has a size larger than that of cauterization loop 94 so that a simultaneous retraction of the two loops 94 and 98 into the distal end of tubular member 92 results in a completed contraction of cauterization loop 94 while a portion of auxiliary loop 98 still remains outside of the tubular member. The difference in the sizes of cauterization loop 94 and auxiliary loop 98 minimize contact between the loops and thus reduces the transmission of heat energy to the auxiliary loop and to pouch 96. Pouch 96 is attached directly to auxiliary loop 98 only and is at most indirectly to cauterization loop 94. With respect to the sizes of loops 94 and 98, auxiliary loop 98 has a circumference (distance around the loon) that is significantly larger than the circumference of cauterization loop 94, so that a portion of the auxiliary loop can remain outside tubular member 92 (together with at least a portion of pouch 96 and a captured polyp) after a completed retraction of cauterization loop 94 into the tubular member during a simultaneous retracting of both loops into the tubular member. As shown in FIG. 5, pouch 96 is attached to auxiliary loop 98 about the circumference thereof and is not attached to cauterization loop 94 about any portion of the circumference of loop 94.

Cauterization loop 94 is provided at the distal end of an electrically conductive push rod or wire 100, whereas auxiliary loop 98 is attached to the distal end of an ancillary elongate connector element or push rod 102. Wire 100 and rod 102 pass through respective channels 104 and 106 defined in tubular member 92 by a partition member 108.

As indicated by dashed or phantom lines 109 in FIG. 5, auxiliary loop 98 may be bent or arced at a distal end 110 so as cup the distal end of cauterization loop 94 and facilitate or enhance polyp capture operations.

Figure 6:
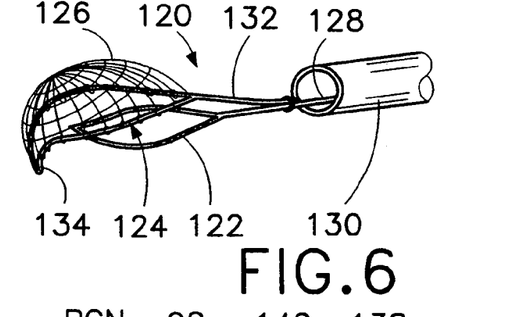
FIG. 6 is a schematic perspective view of yet another cauterization snare assembly in accordance with the present invention.

In a modified cauterization snare assembly 120 illustrated in FIG. 6, a cauterization loop 122 and an auxiliary loop 124 carrying a pouch 126 are connected to a common wire 128 slidably extending through a tubular member 130. Thus, loops 122 and 124 are simultaneously ejected and retracted by manipulation of wire 128. A connector fiber 132 extends from auxiliary loop 124 to wire 128. That connector fiber and auxiliary loop 124 may be made of a heat resistant material such as nylon or coated with a heat resistant material. Thus, at least a portion of auxiliary loop 124 is made of a heat resistant material such as nylon. Auxiliary loop 124 is bent or arced at a distal end 134 so as cup the distal end of cauterization loop 122 and facilitate or enhance polyp capture operations. Pouch 126 is attached directly to auxiliary loop 124 only and is at most indirectly to cauterization loop 122 (via common wire 128). With respect to the sizes of loops 122 and 124, auxiliary loop 124 has a circumference (distance around the loop) that is significantly larger than the circumference of cauterization loop 122, so that a portion of the auxiliary loop can remain outside tubular member 130 (together with at least a portion of pouch 126 and a captured polyp) after a completed retraction of cauterization loop 122 into the tubular member during a simultaneous retracting of both loops into the tubular member. As shown in FIG. 6, pouch 126 is attached to auxiliary loop 124 about the circumference thereof and is not attached to cauterization loop 122 about any portion of the circumference of loop 122.

Cauterization loops 94 and 122 and the respective auxiliary loops 98 and 124 are at least approximately coplanar in the illustrated expanded configurations the loops assume upon ejection from the respective tubular member 92 and 130. Generally, the loops 94, 122 and 98, 124 are biased by internal spring forces to assume the expanded configurations upon release from the tubular members 92 and 130.

Figure 7A:
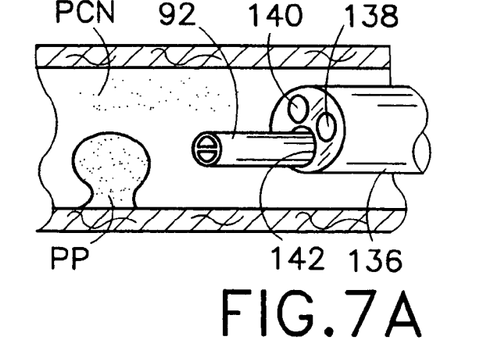
FIGS. 7A through 7F are partially cross-sectional views of a patient's colon and partially schematic perspective views of an endoscope employing the cauterization snare assembly of FIG. 5, showing successive steps in a polyp retrieval method pursuant to the invention.
Figure 7B:
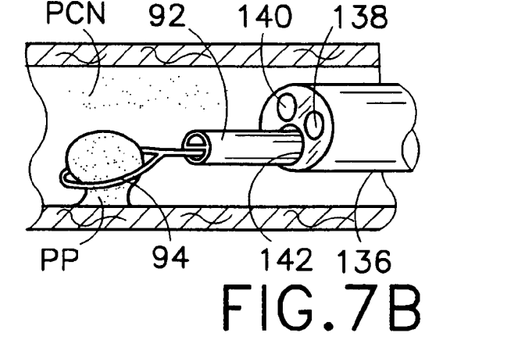
Figure 7C:
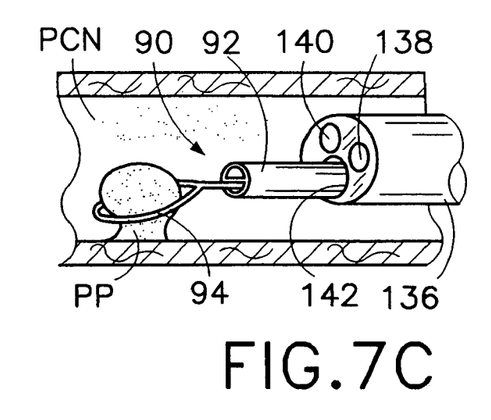
Figure 7D:
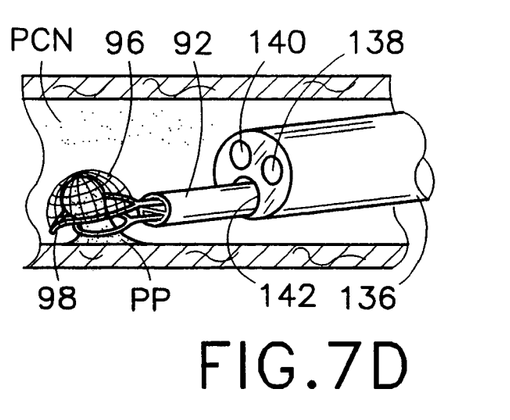
Figure 7E:
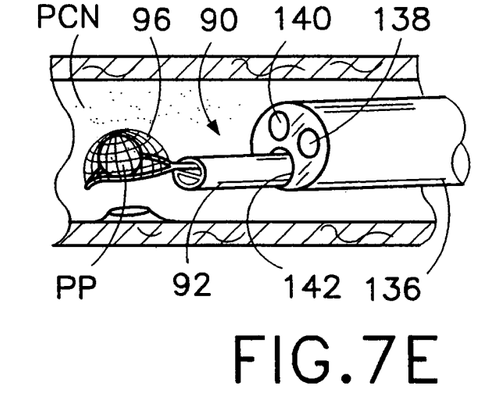
Figure 7F:
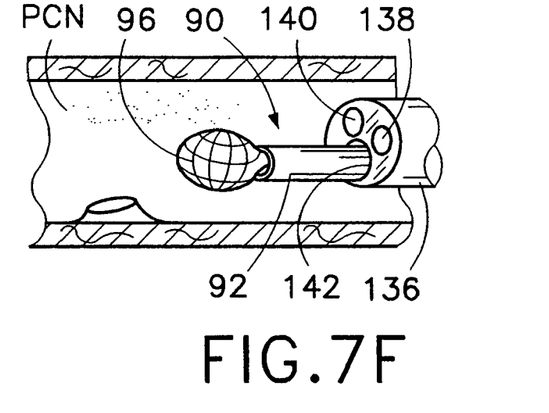

FIGS. 7A through 7F illustrate successive steps in the utilization of snare assembly 90 in a minimally invasive polyp removal operation. FIGS. 7D through 7F are applicable to the use of snare assembly 120. A distal end portion of an endoscope insertion member 136 is inserted into a patient's colon PCN until a polyp PP is detected via endoscope optics 138 and 140 (FIG. 7A). At that juncture, tubular member 92 is shifted by a user in a distal direction to eject a distal end portion of the tubular member from a biopsy channel 142 of the endoscope insertion member 136. Subsequently, electrically conductive element or wire 100 is pushed in the distal direction to eject cauterization loop 94 from tubular member 92 (FIG. 7B), the cauterization loop expanding from a collapsed configuration into an at least partially opened configuration upon escape from the tubular member. The instrument assembly is manipulated by the user to place cauterization loop 94 over the polyp PP (FIG. 7B) and to tighten the cauterization loop about the polyp PP (FIG. 7C). Connector element or push rod 102 is then shifted to eject auxiliary loop 98 from tubular member 92 (FIG. 7D). Upon this ejection, auxiliary loop 98 expands from a collapsed configuration into an at least partially opened configuration. Thereafter, the instrument assembly 90 is manipulated to pass the expanded auxiliary loop 98 over polyp PP. Electrically conductive element or wire 100 and connector element or push rod 102 may be simultaneously pulled to draw cauterization loop 94 and auxiliary loop 98 into the distal end portion of tubular member 92, thereby contracting the cauterization loop and the auxiliary loop. An electrical current is passed through cauterization loop 94 during the pulling of wire 100 and push rod 102 and the contracting of cauterization loop 94 and auxiliary loop 98, thereby severing polyp PP. The severed polyp PP is caught in the pouch 96 upon a partial closure thereof owing to drawing of auxiliary loop 98 into the distal end portion of tubular member 92. A portion of auxiliary loop 98 remains outside of tubular member 92 after cauterization loop 94 has been completely withdrawn into the distal end portion of the tubular member.

As shown in FIG. 3, snare assembly 50, as well as any of the snare assemblies disclosed herein, may be provided with at least one and preferably two flexible tensile members or tethers 150 and 152 connected to pouch 52 at proximal end points 154 thereof. Flexible tensile members 150 and 152 are also connected to tubular member 72 at a pair of holes 158 and 160 formed in tubular member 72 at points spaced from a distal end thereof. Tensile members 150 and 152 extend from flexible pouch 52 into tubular member 72. Tensile members 150 and 152 are segments of a single flexible tensile tether member (not separately designated which extends through holes 158 and 160 in tubular member 72. A patch (not shown) may be disposed on an outer surface of tubular member 72 over holes 158 and 160 and over a bight portion 162 of the single tensile member which is located outside the tubular member. The patch is a thin film of polymeric material which is heat shrunk tightly over the tubular member 72. The patch ensures that bight portion 162 is not snagged on possible protuberances inside the endoscope biopsy channel 76 (FIGS. 4A–4D).

When cauterization loop 54 is ejected from tubular member 72, pouch or capture pocket 52 slides along loop 54, staying outside of the tubular member, as illustrated in FIG. 4D. In the event that the loop 54 is subsequently ejected again from the distal end of tubular member 72, tensile segments 150 and 152 hold the proximal end of pouch or capture pocket 52 so that the pouch slides back along the emerging loop 54 to become repositioned along the loop as illustrated in FIG. 3.

The tensile tether members 150 and 152 ensures that the pouch 52 can remain outside the tubular member 72 and yet can be reopened or repositioned in the event it is necessary or desirable to eject the loop 54 again. If tensile segments 150 and 152 were attached to loop 54 or wire 73, as it is in some prior art pouches, a polyp contained in pouch or capture pocket 52 would be mashed owing to a dragging of the pocket and its contents into tubular member 72.

It is to be noted that any of the pouches or capture pockets disclosed herein are preferably provided with at least one and preferably two flexible tensile members or tethers for this redeployment purpose. This feature of the present cauterization snare assemblies is disclosed in U.S. Pat. No. 5,759,187.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. In a medical cauterization snare assembly comprising a tubular member, an electrically conductive loop ejectable from a distal end of said tubular member, and a capture pouch also ejectable from said distal end of said tubular member, said loop being a first loop having a first size, the improvement wherein said pouch is attached to a second loop having a second size larger than said first size so that a simultaneous retraction of said first loop and said second loop into said distal end of said tubular member results in a completed retraction of said first loop while a portion of said second loop still remains outside of said tubular member.

2. The snare assembly set forth in claim 1 wherein said first loop and said second loop are both connected to a common wire slidably extending through said tubular member, at least a portion of said second loop being made of a heat resistant material.

3. The snare assembly set forth in claim 2 wherein said heat resistant material is nylon.

4. The snare assembly set forth in claim 1 wherein said first loop and said second loop are at least approximately coplanar in an expanded configuration upon ejection from said tubular member.

5. The snare assembly set forth in claim 4 wherein said second loop is bent out of a planar configuration.

6. The snare assembly set forth in claim 1 wherein said second loop is bent out of a planar configuration.

7. A medical cauterization snare assembly comprising:
a tubular member;
an elongate electrically conductive element slidably disposed at least partially in said tubular member;
a first loop having a first circumference and made of an electrically conductive material and provided at one end of said electrically conductive element for alternate ejection from and retraction into a distal end of said tubular member;
a second loop having a second circumference larger than said first circumference so that a simultaneous retraction of said first loop and said second loop into said distal end of said tubular member results in a completed retraction of said first loop while a portion of said second loop still remains outside of said tubular member;
an elongate connector element, said second loop being formed at one end of said connector element whereby said second loop is alternately ejected from and retracted into said tubular member; and
a pouch member attached to said second loop along at least a portion of said second circumference so as to form a capture pocket with said second loop defining a mouth or opening of said capture pocket, said first loop being free all along said first circumference of attachment to said pouch member.

8. The snare assembly set forth in claim 7 wherein at least a portion of said second loop being made of a heat resistant material and wherein said connector element is attached to said electrically conductive element.

9. The snare assembly set forth in claim 7 wherein said first loop and said second loop are at least approximately coplanar in an expanded configuration upon ejection from said tubular member.

10. The snare assembly set forth in claim 7 wherein said second loop is bent out of a planar configuration.

11. A minimally invasive surgical method comprising:
(a) providing a medical treatment assembly including:
a tubular member;
an elongate electrically conductive element slidably disposed at least partially in said tubular member;
a first loop having a first circumference and made of an electrically conductive material and provided at one end of said electrically conductive element for alternate ejection from and retraction into a distal end of said tubular member;
a second loop made at least partially of a heat resistant material, said second loop having a second circumference larger than said first circumference so that a simultaneous retraction of said first loop and said second loop into said distal end of said tubular member results in a completed retraction of said first loop while a portion of said second loop still remains outside of said tubular member;
an elongate connector element, said second loop being formed at one end of said connector element whereby said second loop is alternately ejected from and retracted into said tubular member; and
a pouch member attached to said second loop along at least a portion of said second circumference so as to form a capture pocket with said second loop defining a mouth or opening of said capture pocket, said first loop being free all along said first circumference of attachment to said pouch member;

(b) inserting a distal end portion of said tubular member into a patient;
(c) after the inserting of said distal end portion of said tubular member into the patient, pushing said electrically conductive element to eject said first loop from said tubular member, said first loop expanding from a collapsed configuration into an at least partially opened configuration upon ejection of said first loop from said tubular member;
(d) after the inserting of said distal end portion of said tubular member into the patient, pushing said connector element to eject said second loop from said tubular member, said second loop expanding from a collapsed configuration into an at least partially opened configuration upon ejection of said second loop from said tubular member;
(e) manipulating said tubular member and said electrically conductive element to pass the expanded first loop and the expanded second loop over a lump of tissue inside the patient;
(f) after the passing of the expanded first loop and the expanded second loop over said lump of tissue, pulling said electrically conductive element and said connector element to simultaneously draw said first loop and said second loop into said distal end portion of said tubular member, thereby contracting said first loop and said second loop;
(g) passing an electrical current through said first loop during the pulling of electrically conductive element and said connector element and the contracting of said first loop and said second loop, thereby severing said lump of tissue;
(h) capturing the severed lump of tissue in said capture pocket upon a partial closure thereof owing to drawing of said second loop into said distal end portion of said tubular member; and
(i) maintaining a portion of said second loop outside of said tubular member after a completed withdrawing of said first loop into said distal end portion of said tubular member.

12. A medical device comprising:
a tubular member;
an electrically conductive loop ejectable from a distal end of said tubular member; and
a capture pouch also ejectable from said distal end of said tubular member, said tubular member, said electrically conductive loop, and said pouch being adapted to enable retrieval of multiple tissue samples from a patient, said pouch being attached to an auxiliary loop, said auxiliary loop having a substantially larger circumference than a circumference of said electrically conductive loop so that a simultaneous retraction of said first loop and said second loop into said distal end of said tubular member results in a completed retraction of said first loop while a portion of said second loop still remains outside of said tubular member.

13. In a medical cauterization snare assembly comprising a tubular member, an electrically conductive loop ejectable from a distal end of said tubular member, and a capture pouch also ejectable from said distal end of said tubular member, said loop being a first loop having a first size, the improvement wherein said pouch is attached to a second loop having a second size larger than said first size so that a simultaneous retraction of said first loop and said second loop into said distal end of said tubular member results in a completed contraction of said first loop while a portion of said second loop still remains outside of said tubular member, said first loop and said second loop being at least approximately coplanar in an expanded configuration upon ejection from said tubular member.

14. The snare assembly set forth in claim 13 wherein said first loop and said second loop are both connected to a common wire slidably extending through said tubular member, at least a portion of said second loop being made of a heat resistant material.

15. The snare assembly set forth in claim 14 wherein said heat resistant material is nylon.

16. The snare assembly set forth in claim 13 wherein said second loop is bent out of a planar configuration.

* * * * *